(12) United States Patent
Izad

(10) Patent No.: US 10,614,052 B2
(45) Date of Patent: *Apr. 7, 2020

(54) DATA STANDARDIZATION AND VALIDATION ACROSS DIFFERENT DATA SYSTEMS

(71) Applicant: International Business Machines Corporation, Armonk, NY (US)

(72) Inventor: Olivier Izad, Chagrin Falls, OH (US)

(73) Assignee: International Business Machines Corporation, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/213,137

(22) Filed: Dec. 7, 2018

(65) Prior Publication Data
US 2019/0108164 A1    Apr. 11, 2019

Related U.S. Application Data

(63) Continuation of application No. 15/152,966, filed on May 12, 2016, now Pat. No. 10,169,436.

(51) Int. Cl.
| | |
|---|---|
| *G06F 16/30* | (2019.01) |
| *G06F 16/23* | (2019.01) |
| *G06F 16/25* | (2019.01) |
| *G06F 16/24* | (2019.01) |
| *G16H 10/60* | (2018.01) |

(52) U.S. Cl.
CPC ............. *G06F 16/23* (2019.01); *G06F 16/24* (2019.01); *G06F 16/258* (2019.01); *G16H 10/60* (2018.01)

(58) Field of Classification Search
CPC combination set(s) only.
See application file for complete search history.

(56) References Cited

U.S. PATENT DOCUMENTS

| | | |
|---|---|---|
| 8,688,468 B1 | 4/2014 | daCosta |
| 9,002,875 B2 | 4/2015 | Gopalakrishnan et al. |
| 9,243,906 B1 | 1/2016 | Conrad |

(Continued)

OTHER PUBLICATIONS

Article entitled "The Data Curation Process", by IBM, dated 2016.*
(Continued)

*Primary Examiner* — Mahesh H Dwivedi
(74) *Attorney, Agent, or Firm* — Ryan Lewis; Edell, Shapiro & Finnan, LLC

(57) ABSTRACT

A system standardizes and validates data across source systems and includes at least one processor. The system converts a value of a physiological attribute of an entity to a standardized value, and dynamically determines a first value range for the physiological attribute from a corresponding region of clustered physiological data of a population. The first value range is specific to and varies with an age of the entity. The standardized value of the physiological attribute is compared to the first value range, and the standardized value of the physiological attribute is designated as an outlier in response to the standardized value of the physiological attribute residing outside of the first value range. Embodiments of the present invention further include a method and computer program product for standardizing and validating data across source systems in substantially the same manner described above.

18 Claims, 13 Drawing Sheets

(56) References Cited

U.S. PATENT DOCUMENTS

| | | | |
|---|---|---|---|
| 2007/0178501 | A1 | 8/2007 | Rabinowitz et al. |
| 2011/0153346 | A1 | 6/2011 | Jokinen |
| 2011/0235886 | A1 | 9/2011 | Kelly |
| 2011/0288886 | A1 | 11/2011 | Whiddon |
| 2013/0047113 | A1 | 2/2013 | Hume |
| 2014/0032240 | A1 | 1/2014 | Lougheed et al. |
| 2014/0108024 | A1 | 4/2014 | Evans |
| 2016/0267224 | A1 | 9/2016 | Natarajan |
| 2017/0052970 | A1* | 2/2017 | Crabtree ............... G06F 16/254 |
| 2017/0124216 | A1* | 5/2017 | Miller .................. G06F 16/285 |
| 2017/0329832 | A1 | 11/2017 | Izad |
| 2018/0122499 | A1 | 5/2018 | Austin et al. |

OTHER PUBLICATIONS

Article entitled "IBM Explorys Life Sciences", by IBM, dated May 2016.*

Article entitled "IBM Explorys Cohort Discovery, IBM Explorys Therapeutic Datasets, and IBM Explorys Virtual Workbench provide life sciences insights into realworld care delivery", by IBM, dated May 3, 2016.*

"Clinical Growth Charts", Centers for Disease Control and Prevention, http://www.cdc.gov/growthcharts/clinical_charts.htm, last updated Aug. 4, 2009, 10 pages.

List of IBM Patents or Patent Applications Treated as Related, Dec. 2018, 1 page.

"The Explorys Platform", IBM Watson Health, Solution Brief, Produced in the United States of America, Nov. 2015, 4 pages.

\* cited by examiner

US 10,614,052 B2

DATA STANDARDIZATION AND VALIDATION ACROSS DIFFERENT DATA SYSTEMS

CROSS-REFERENCE TO RELATED APPLICATIONS

This application is a continuation of U.S. patent application Ser. No. 15/152,966, entitled "DATA STANDARDIZATION AND VALIDATION ACROSS DIFFERENT DATA SYSTEMS" and filed May 12, 2016, the disclosure of which is incorporated herein by reference in its entirety.

BACKGROUND

1. Technical Field

Present invention embodiments relate to data integration for a plurality of data systems, and more specifically, to integrating, standardizing, and validating medical data for patients based on criteria dynamically determined from physiological conditions at various life stages of the patients. In addition, outliers are further detected within the standardized data to validate the data and enhance data quality for downstream processing of analytics.

2. Discussion of the Related Art

Healthcare networks have very complicated organization structures. An organization typically comprises multiple source systems (e.g., a source of electronic medical records including electronic health records (EHR), records from a claims system, lab feed, various data sources implementing the HL7 standard, patient satisfaction survey, etc.). Clinically integrated networks (CIN) or galaxies (e.g., a group of organizations) are collections of individual healthcare systems with data sharing agreements. Analytics may be applied to the various electronic medical records to produce results for a desired population (e.g., of patients, health care providers, provider organizations or networks, etc.) based upon queries by end users.

In order to provide a set of analytics, the medical records undergo a normalization process that subjects the medical records to a standard from an appropriate medical ontology. For example, the term "Diabetes Mellitus" within a medical record is normalized to the following target codes: SNOMED ID: 73211009, ICD9: 250, ICD10: E08, while the term "Red Blood Cell Counts" within a medical record is normalized to the code LOINC ID: "26453-1". Meaningful analytics are dependent upon the correctness of these normalized data points. By way of example, one particular attribute often used in predictive measures is Body Mass Index (BMI). BMI is a metric calculated using a patient clinical height and weight, and indicates a patient body type and obesity level. This metric is often used for calculating risk scores or predictive analytics. Whenever a height or weight record is erroneous, an inaccurate BMI ensues, and these errors further cascade into the analytics being calculated.

Another metric used in determining medical decisions is Body Surface Area (BSA). Drugs and prescription dosages are determined proportionally to a patient size. Currently, a common method to estimate size is by calculating a patient BSA. Similar to BMI, BSA is dependent upon a patient height and weight, and the BSA validity is also dependent on the accuracy of the height and weight records. An inaccurate BSA may lead to erroneous prescriptions which could provide lethal overdoses in a severe case, or insufficient dosages that cause a perpetual lingering of a disease.

SUMMARY

According to one embodiment of the present invention, a system standardizes and validates data across source systems and includes at least one processor. The system converts a value of a physiological attribute of an entity to a standardized value, and dynamically determines a first value range for the physiological attribute from a corresponding region of clustered physiological data of a population. The first value range is specific to and varies with an age of the entity. The standardized value of the physiological attribute is compared to the first value range, and the standardized value of the physiological attribute is designated as an outlier in response to the standardized value of the physiological attribute residing outside of the first value range. Embodiments of the present invention further include a method and computer program product for standardizing and validating data across source systems in substantially the same manner described above.

BRIEF DESCRIPTION OF THE DRAWINGS

Generally, like reference numerals in the various figures are utilized to designate like components.

DETAILED DESCRIPTION

Figure 1:
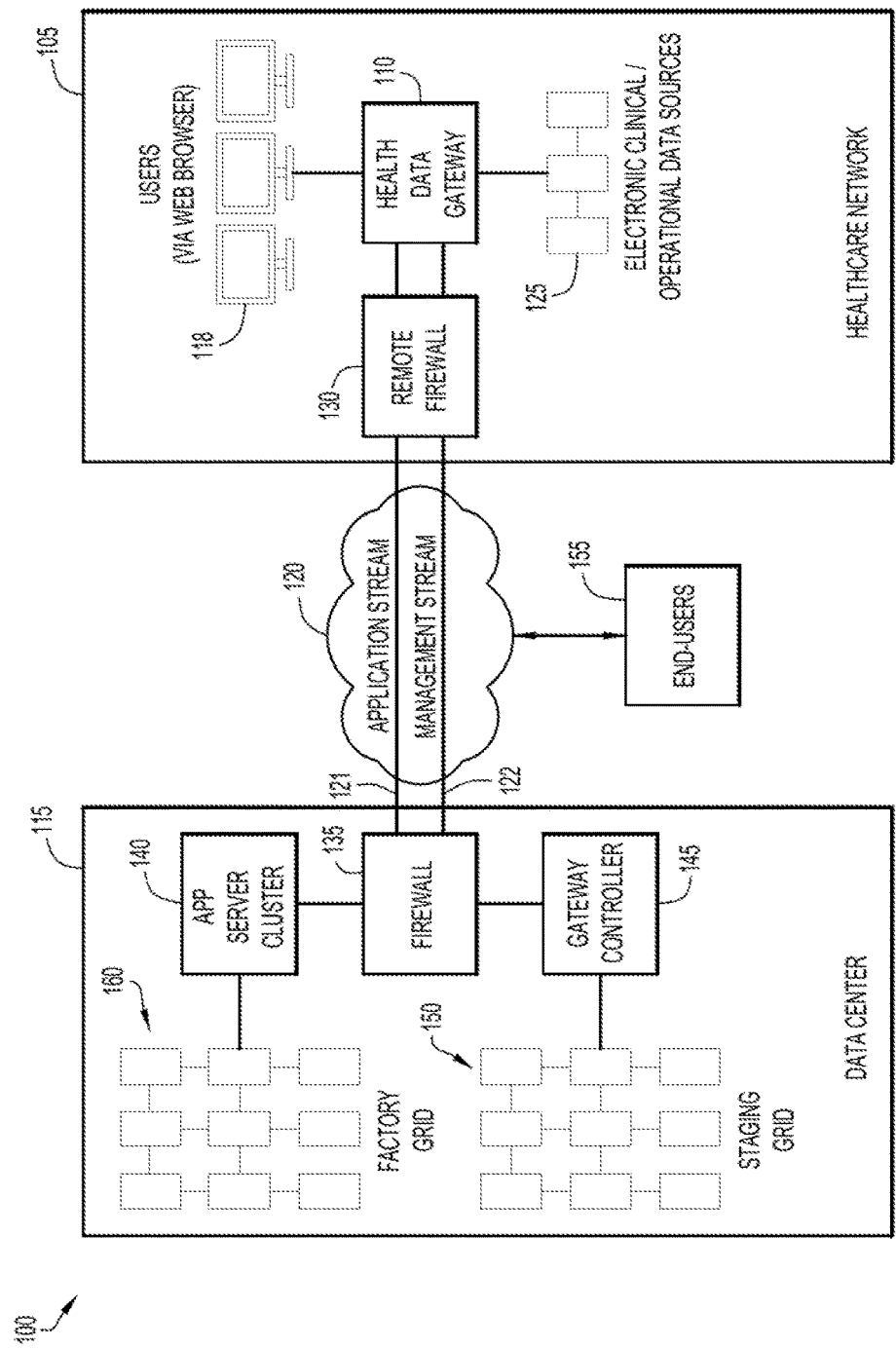
FIG. 1 is a diagrammatic illustration of an example computing environment according to an embodiment of the present invention.

Present invention embodiments integrate, standardize, and validate medical data for patients based on criteria dynamically determined from physiological conditions at various life stages of the patients. In addition, outliers are further detected within the standardized data to provide clean data for accurate analytics.

For example, clinical height and weight values are often entered as encounters or observation tables with units of measure being provided occasionally. These are typically entered manually which leads to errors. There are various types of errors, with common ones including the following:

entering an incorrect unit (e.g., Height: 6 inches instead of 6 feet, Height: 1' 80" instead of 1.80 m, Weight: 80 lbs instead of 80 kg, etc.);

removing a decimal point (e.g., Weight: 1805 lbs instead of 180.5 lbs, Height: 1645 cm instead of 164.5 cm, etc.);

substituting a keystroke with a neighboring key (e.g., Height: 5; 11 instead of 5' 11, Weight: 180/5 lbs instead of 180.5 lbs, etc.);

localization errors (e.g., a comma to denote decimal digits instead of a period (e.g., Height: 164.5 cm instead of 164.5 cm, Weight: 65.5 kg instead of 65.5 kg, etc.));

confusing a character with a character having a similar appearance (e.g., Height: 6' 1" instead of 6' 1", etc.); and interchanging height and weight records (e.g., Height: 180 lbs instead of Weight: 180 lbs, etc.).

Present invention embodiments employ physiological validation and outlier detection to enhance data quality. Physiological validation ensures a data value is within an appropriate physiological range in order to identify and correct the above inconsistencies. Further, clinical height and weight values include strong dynamic changes throughout the life of a patient to complicate the standardization. This enables the range of legitimate values to vary for patients during various stages of life. Present invention embodiments further employ the outlier detection that considers pediatric growth, geriatric shrinkage, and patient historical data to validate the height and weight values.

Whenever a height or weight record is erroneous, inaccuracies ensue that cascade into the analytics, thereby producing inaccurate, skewed, and effectively useless analytic data. This provides unnecessarily large data sets that waste computer processing (or processor) time and significantly reduce efficiency (due to processing the erroneous data that lead to effectively useless results). Further, the analytics may need to be re-executed by the processor several times until sufficient accuracy of (and/or confidence in) the data is attained, thereby requiring significant additional processing and resources to attain a desired data set. Accordingly, present invention embodiments may remove the erroneous data (e.g., indicated as outliers) from the data set to provide a reduced data set that increases the computer (or processor) processing speed and reduces computer or other resources used for processing the analytics to produce results in reduced time. In addition, enhanced accuracy of data is attained without several re-executions of the analytics by the computer (or processor), thereby further reducing the computer processing (or processor) time and computer or other resources needed to produce results of the analytics.

An example computing environment for use with present invention embodiments is illustrated in FIG. 1. Computing environment 100 includes a healthcare network 105 in communication with a data center 115 over a communications network 120 (e.g., providing a secure virtual private network (VPN)). The communications over network 120 preferably occur between a firewall 130 of healthcare network 105 and a firewall 135 of data center 115. The communications over network 120 may include an application stream 121 pertaining to communications for applications and a management stream 122 pertaining to communications for managing the data. The network may be implemented by any number of any suitable communications media (e.g., wide area network (WAN), local area network (LAN), Internet, Intranet, etc.). Alternatively, healthcare network 105 and data center 115 may be local to each other, and communicate via any appropriate local communication medium (e.g., local area network (LAN), hardwire, wireless link, Intranet, etc.).

Healthcare network 105 includes a health data gateway 110 coupled to end-user systems 118 and one or more clinical/operational data sources 125 providing various medical information (e.g., electronic health records (EHR), records from a claims system, lab feed, various data sources implementing the HL7 standard, patient satisfaction survey, etc.) stored according to a source data model.

Data center 115 includes an application server cluster 140, a gateway controller 145, a staging grid 150, and a factory grid 160. Health data gateway 110 of healthcare network 105 is configured to acquire data from data sources 125 and transmit the acquired data to gateway controller 145 of data center 115. The gateway controller receives the incoming data from the communications network and processes that data to staging grid 150. The staging and factory grids each include a cluster of computer systems to store data and perform parallel processing. By way of example, the staging and factory grids each employ a HADOOP cluster with a HADOOP distributed file system (HDFS).

Staging grid 150 inspects and publishes the data to factory grid 160 in accordance with a data model employed by the factory grid. Factory grid 160 includes various engines to perform desired analytics on the data based on queries received from end-user systems 118 and other end-user systems 155 accessing data center 115 over network 120. The queries are handled in conjunction with application server cluster 140 to produce desired results.

Figure 2:
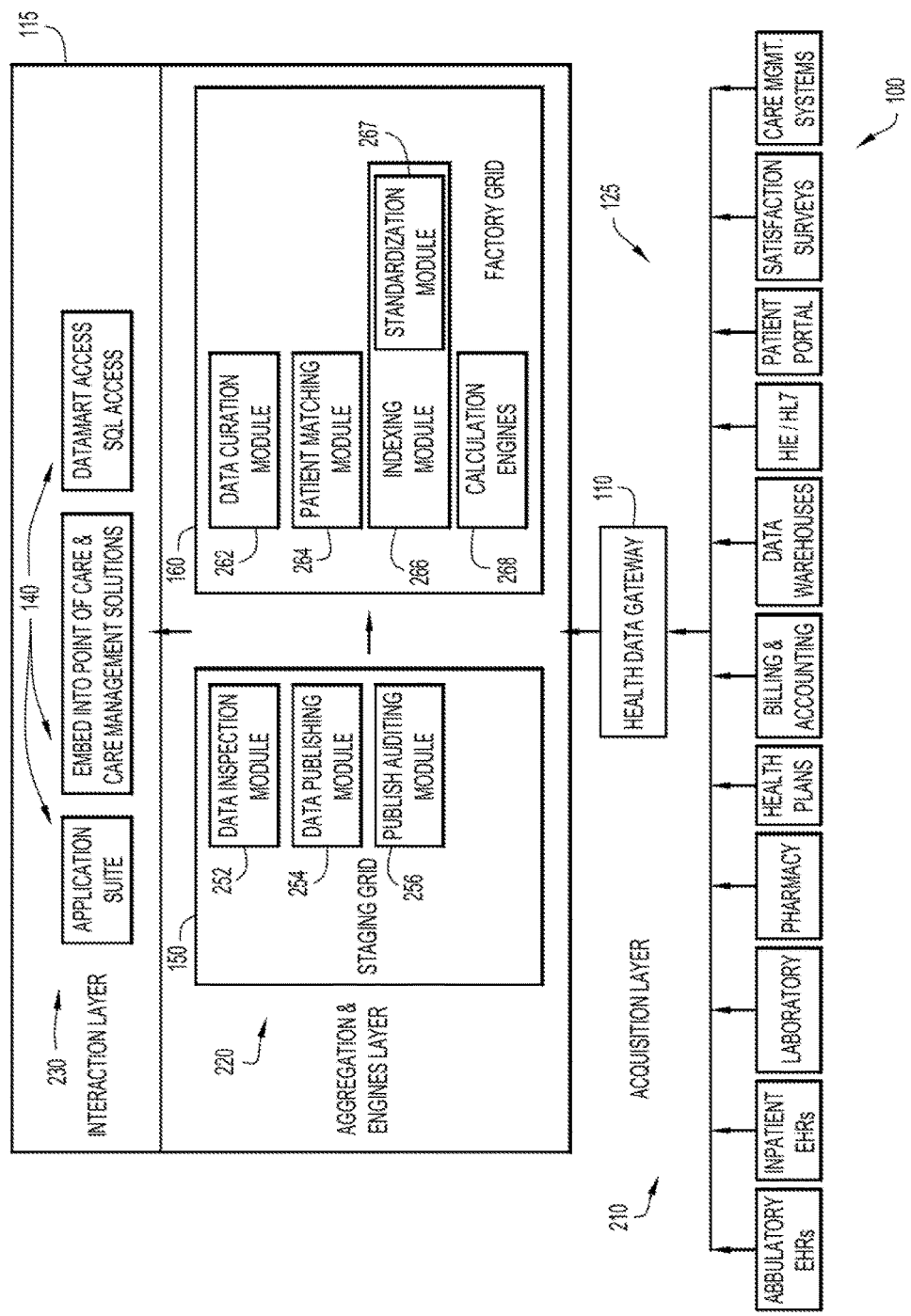
FIG. 2 is a diagrammatic illustration of the data center of the computing environment of FIG. 1 according to an embodiment of the present invention.

Referring to FIG. 2, health data gateway 110 of one or more healthcare networks is configured to acquire data from data sources 125 of those healthcare networks (e.g., ambulatory electronic health records (EHR), inpatient electronic health records (EHR), laboratory data, pharmacy data, health plan data, billing and accounting data, data warehouses, health information exchange (HIE)/HL7 data, patient portal, satisfaction surveys, care management systems, etc.) and transmit the acquired data to gateway controller 145 of data center 115 as described above. The healthcare networks and/or data sources 125 form an acquisition layer 210 providing data to data center 115 via health data gateway 110.

Gateway controller 145 receives the incoming data from communications network 120 and processes that data to staging grid 150 employing data models of the source systems. Staging grid 150 includes a data inspection module 252, a data publishing module 254, and a publish auditing module 256 to inspect, publish, and audit the data to factory grid 160 in accordance with the data model employed by the factory grid.

Factory grid 160 includes a data curation module 262, a patient matching module 264, an indexing module 266, and various calculation/analytic engines 268. Data curation module 262 performs data curation operations including mapping codes, data cleansing, and basic standardization, while patient matching module 264 performs patient matching operations to determine records associated with the same patient. Indexing module 266 performs indexing operations including combining records based on patient matching, mappings, and application of risk models. Indexing module 266 includes a standardization module 267 to standardize data according to present invention embodiments as described below. The calculation/analytic engines perform the desired analytics based on queries received from end-users from an interaction layer 230 enabling application server cluster 140 to provide various applications for processing and accessing the data (e.g., analytic applications, SQL access, etc.). The staging and factory grids form an aggregation and engines layer 220 to process the acquired data, while the queries are handled by factory grid 160 in conjunction with application server cluster 140 to produce desired results for the interaction layer.

The various applications of application server cluster 140 may be provided in a cloud environment. It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones or other devices, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly release to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

Figure 3:
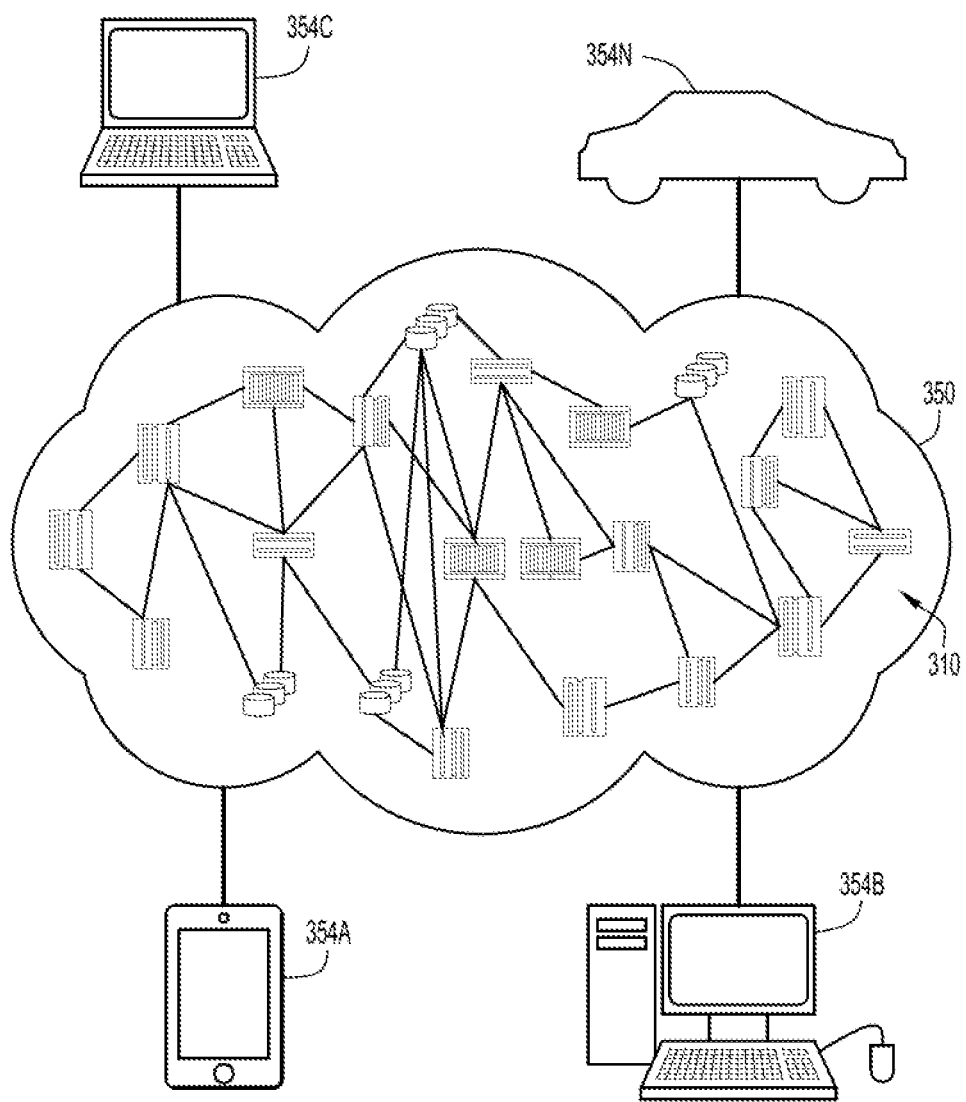
FIG. 3 is a diagrammatic illustration of an example cloud computing environment for the computing environment of FIG. 1 according to an embodiment of the present invention.

A cloud computing environment is service oriented with a focus on statelessness, low coupling, modularity, and semantic interoperability. At the heart of cloud computing is an infrastructure comprising a network of interconnected nodes. Referring now to FIG. 3, illustrative cloud computing environment 350 is depicted. As shown, cloud computing environment 350 comprises one or more cloud computing nodes 310 with which local computing devices used by cloud consumers, such as, for example, personal digital assistant (PDA) or cellular telephone 354A, desktop computer 354B, laptop computer 354C, and/or automobile computer system 354N may communicate. Nodes 310 may communicate with one another. They may be grouped (not shown) physically or virtually, in one or more networks, such as Private, Community, Public, or Hybrid clouds as described hereinabove, or a combination thereof. This allows cloud computing environment 350 to offer infrastructure, platforms and/or software as services for which a cloud consumer does not need to maintain resources on a local computing device. It is understood that the types of computing devices 354A-N shown in FIG. 3 are intended to be illustrative only and that computing nodes 310 and cloud computing environment 350 can communicate with any type of computerized device over any type of network and/or network addressable connection (e.g., using a web browser).

Figure 4:
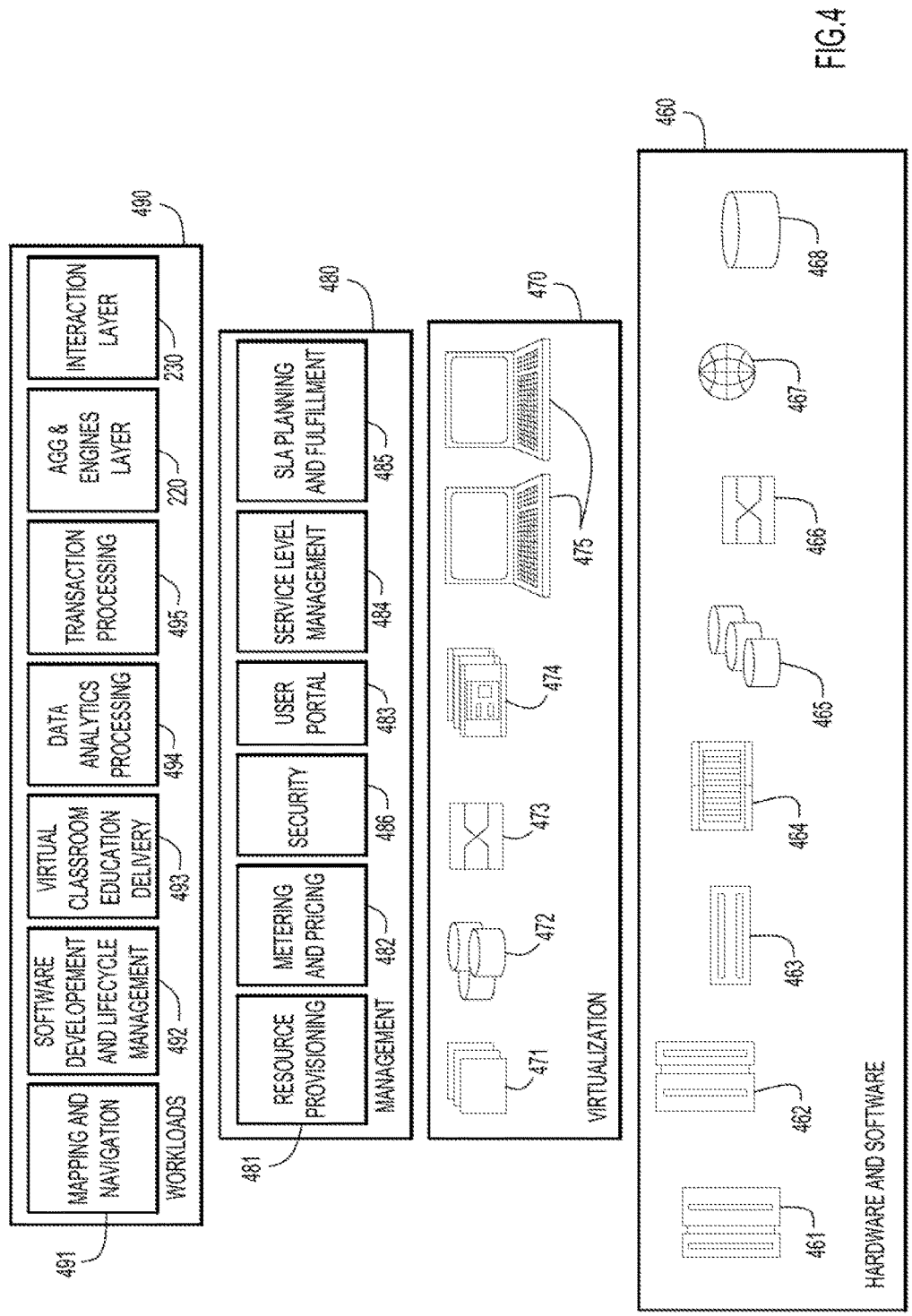
FIG. 4 is a diagrammatic illustration of abstraction model layers according to an embodiment of the present invention.

Referring now to FIG. 4, a set of functional abstraction layers provided by cloud computing environment 350 (FIG. 3) is shown. It should be understood in advance that the components, layers, and functions shown in FIG. 4 are intended to be illustrative only and embodiments of the invention are not limited thereto. As depicted, the following layers and corresponding functions are provided:

Hardware and software layer 460 includes hardware and software components. Examples of hardware components include: mainframes 461; RISC (Reduced Instruction Set Computer) architecture based servers 462; servers 463; blade servers 464; storage devices 465; and networks and networking components 466. In some embodiments, software components include network application server software 467 and database software 468.

Virtualization layer 470 provides an abstraction layer from which the following examples of virtual entities may be provided: virtual servers 471; virtual storage 472; virtual networks 473, including virtual private networks; virtual applications and operating systems 474; and virtual clients 475.

In one example embodiment, management layer 480 may provide some or all of the functions for data center 115 described herein. Resource provisioning 481 provides dynamic procurement of computing resources and other resources that are utilized to perform tasks within the cloud computing environment. Metering and Pricing 482 provide cost tracking as resources are utilized within the cloud computing environment, and billing or invoicing for consumption of these resources. In one example, these resources may comprise application software licenses. Security 486 provides identity verification for cloud consumers and tasks, as well as protection for data and other resources. User portal 483 provides access to the cloud computing environment for consumers and system administrators. Service level management 484 provides cloud computing resource allocation and management such that required service levels are met. Service Level Agreement (SLA) planning and fulfillment 485 provide pre-arrangement for, and procurement of, cloud computing resources for which a future requirement is anticipated in accordance with an SLA.

Workloads layer 490 provides examples of functionality for which the cloud computing environment may be utilized. Examples of workloads and functions which may be provided from this layer include: mapping and navigation 491; software development and lifecycle management 492; virtual classroom education delivery 493; data analytics processing 494; transaction processing 495; aggregation and engines layer 220 (FIG. 2); and interaction layer 230 (FIG. 2).

Figure 5:
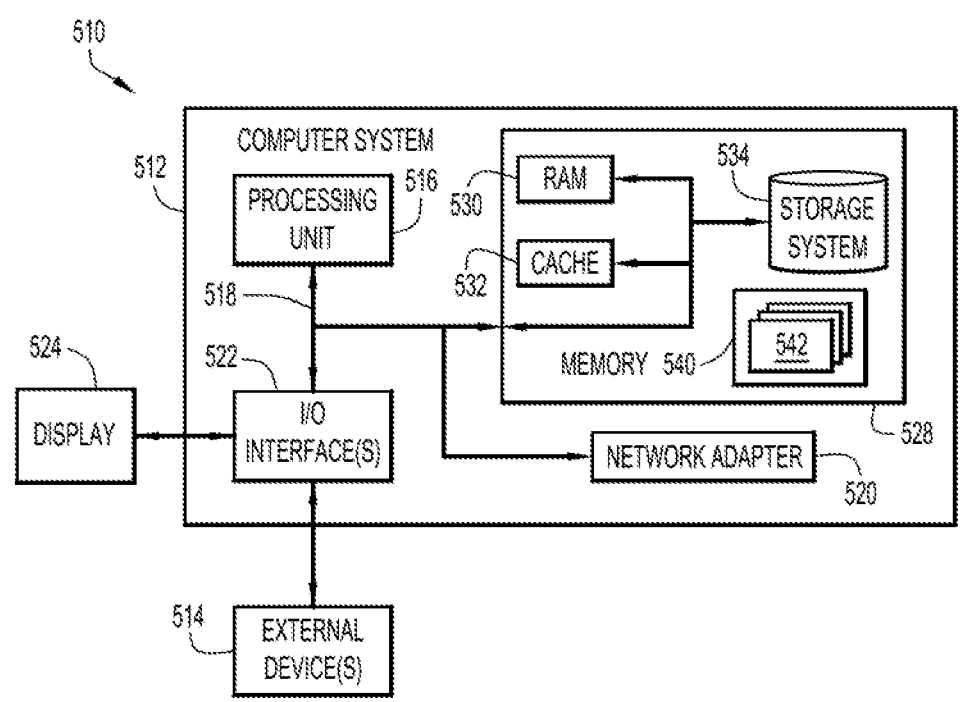
FIG. 5 is a block diagram of a computing node according to an embodiment of the present invention.

Referring now to FIG. 5, a schematic of an example of a computing node or device 510 of computer environment 100 (e.g., health data gateway 110, application server cluster 140, gateway controller 145, computing nodes of staging grid 150, computing nodes of factory grids 160, etc.) and cloud environment 350 (e.g., cloud computing node 310, etc.) is shown. The computing node or device is only one example of a suitable computing node for computing environment 100 and cloud computing environment 350 and is not intended to suggest any limitation as to the scope of use or functionality of embodiments of the invention described herein. Regardless, computing node 510 is capable of being implemented and/or performing any of the functionality set forth herein.

In computing node 510, there is a computer system 512 which is operational with numerous other general purpose or special purpose computing system environments or configurations. Examples of well-known computing systems, environments, and/or configurations that may be suitable for use with computer system 512 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system 512 may be described in the general context of computer system executable instructions, such as program modules, being executed by a computer system. Generally, program modules may include routines, programs, objects, components, logic, data structures, and so on that perform particular tasks or implement particular abstract data types. Computer system 512 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 5, computer system 512 is shown in the form of a general-purpose computing device. The components of computer system 512 may include, but are not limited to, one or more processors or processing units 516, a system memory 528, and a bus 518 that couples various system components including system memory 528 to processor 516.

Bus 518 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system 512 typically includes a variety of computer system readable media. Such media may be any available media that is accessible by computer system 512, and it includes both volatile and non-volatile media, removable and non-removable media.

System memory 528 can include computer system readable media in the form of volatile memory, such as random access memory (RAM) 530 and/or cache memory 532. Computer system 512 may further include other removable/non-removable, volatile/non-volatile computer system storage media. By way of example only, storage system 534 can be provided for reading from and writing to a nonremovable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 518 by one or more data media interfaces. As will be further depicted and described below, memory 528 may include at least one program product having a set (e.g., at least one) of program modules that are configured to carry out the functions of embodiments of the invention.

Program/utility 540, having a set (at least one) of program modules 542, may be stored in memory 528 by way of example, and not limitation, as well as an operating system, one or more application programs, other program modules, and program data. Each of the operating system, one or more application programs, other program modules, and program data or some combination thereof, may include an implementation of a networking environment. Program modules 542 generally carry out the functions and/or methodologies of embodiments of the invention as described herein.

Computer system 512 may also communicate with one or more external devices 514 such as a keyboard, a pointing device, a display 524, etc.; one or more devices that enable a user to interact with computer system 512; and/or any devices (e.g., network card, modem, etc.) that enable computer system 512 to communicate with one or more other computing devices. Such communication can occur via Input/Output (I/O) interfaces 522. Still yet, computer system 512 can communicate with one or more networks such as a local area network (LAN), a general wide area network (WAN), and/or a public network (e.g., the Internet) via network adapter 520. As depicted, network adapter 520 communicates with the other components of computer system 512 via bus 518. It should be understood that although not shown, other hardware and/or software components could be used in conjunction with computer system 512. Examples, include, but are not limited to: microcode, device drivers, redundant processing units, external disk drive arrays, RAID systems, tape drives, and data archival storage systems, etc.

Figure 6:
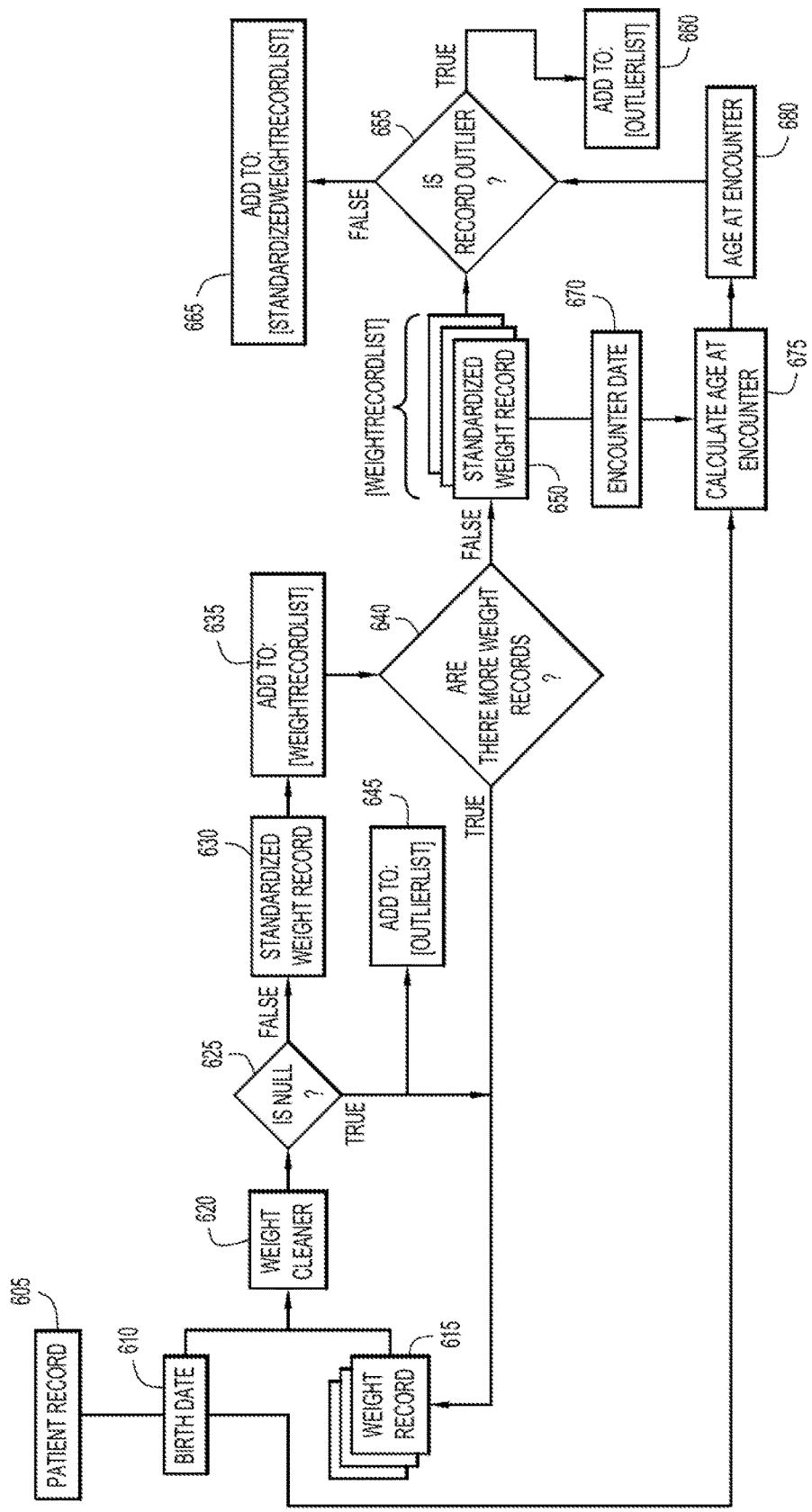
FIG. 6 is a flow diagram illustrating a manner of standardizing and validating medical records according to an embodiment of the present invention.

A manner of cleaning, standardizing, and detecting outliers for medical records (e.g., via factory grid 160 and standardization module 267) is illustrated in FIG. 6. By way of example, the standardization and validation technique of a present invention embodiment is described with respect to standardizing and validating patient weight values. However, present invention embodiments may be utilized to standardize and validate other physiological patient attributes (e.g., height, etc.) in substantially the same manner described below.

The technique of a present invention embodiment utilizes information from a patient (e.g., date of birth, etc.) and a set of corresponding historical patient weight records. The birth date is used to calculate an age of the patient at each encounter where a weight value was recorded. The technique ensures that the weight values are physiologically sound, and that these values are consistent for the patient based on historical data as described below.

Figure 7:
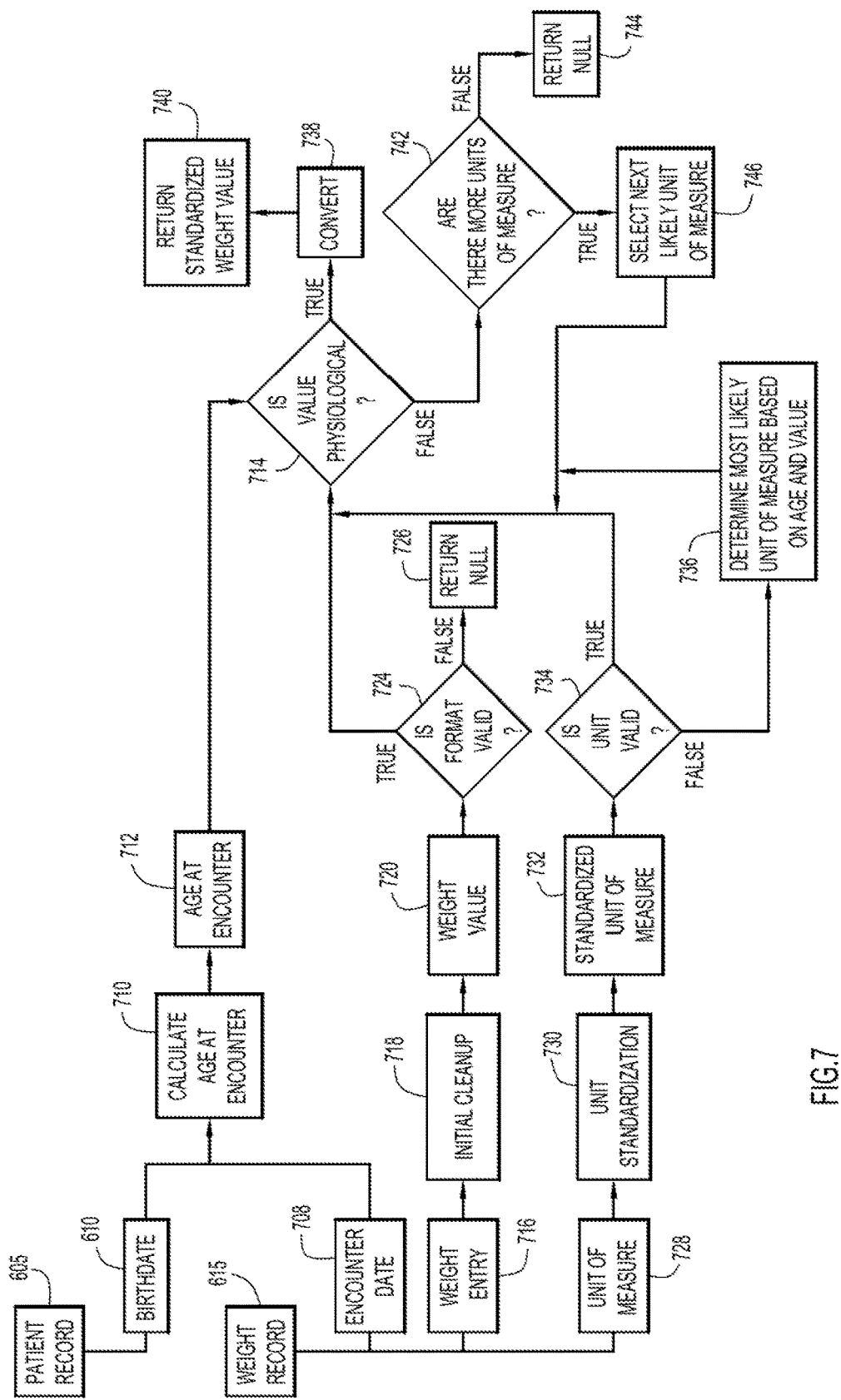
FIG. 7 is a flow diagram illustrating a manner of cleansing data according to an embodiment of the present invention.

In particular, a patient record 605 is retrieved (e.g., from the patient records within factory grid 160, from another data source, etc.), and a date of birth 610 for the patient is determined from the retrieved record. The patient record is associated with a set of weight records 615 each containing a weight measurement for the patient, a time (e.g., an encounter date, etc.) when that weight measurement was obtained, and a unit of measure. The birth date is utilized at step 620 to cleanse and standardize a weight measurement of a weight record as described below (FIG. 7). When the weight measurement cannot be standardized as determined at step 625 (e.g., a resulting standardized weight record contains a null value for the standardized weight measurement), the weight record is indicated as an outlier (or erroneous) and added to an outlier list at step 645 and the next weight record from set of weight records 615 is retrieved for cleansing and standardization of the weight measurement.

When the weight measurement of the weight record is standardized (e.g., the resulting standardized weight record includes a standardized value for the weight measurement) as determined at step 625, the standardized weight record is added to a list at step 635. The standardized weight record includes the standardized weight measurement, the corresponding encounter date, and a unit of measure. The above process is repeated until each of the weight records 615 in the set have been processed as determined at step 640, thereby producing a list of standardized weight records 650.

An encounter date is determined from a standardized weight record 650 at step 670, and an age of the patient 680 at the encounter date (or time of weight measurement) is determined at step 675 (e.g., from the difference between the encounter date and the patient birth date). The standardized weight record and age of the patient are utilized to validate the standardized weight measurement of the standardized weight record based on an outlier detection as described below (e.g., for FIGS. 9 and 10). When the standardized weight measurement is an outlier as determined at step 655, the standardized weight record is indicated as an outlier (or erroneous) and added to the outlier list at step 660. If the standardized weight measurement is valid as determined at step 655, the standardized weight record is added to a valid weight record list at step 665. The above process is repeated until each of the standardized weight records 650 in the list have been processed.

Whenever a medical record is erroneous, inaccuracies ensue that cascade into analytics, thereby producing inaccurate, skewed, and effectively useless analytic data. This provides unnecessarily large data sets that waste computer processing (or processor) time and significantly reduce efficiency (due to processing the erroneous data that leads to effectively useless results). Further, the analytics may need to be re-executed by the processor several times until sufficient accuracy of (and/or confidence in) the data is attained, thereby requiring significant additional processing and resources to attain a desired data set. Accordingly, present invention embodiments may remove the erroneous data (e.g., indicated as outliers) from the data set to provide a reduced data set that increases the computer (or processor) processing speed and reduces computer or other resources used for processing the analytics to produce results in reduced time. In addition, enhanced accuracy of data is attained without several re-executions of the analytics by the computer (or processor), thereby further reducing the computer processing (or processor) time and computer or other resources needed to produce results of the analytics.

A manner of cleansing the weight records (e.g., via factory grid 160 and standardization module 267) according to an embodiment of the present invention (e.g., step 620 of FIG. 6) is illustrated in FIG. 7. Initially, each of the weight records is analyzed, and processed to clean the weight record from common orthographical mistakes (e.g., misplaced characters, localization errors, etc.). Once the records are clean, the technique determines whether the weight measurements are within a physiological region determined by the purported unit of measure. If a unit of measure is not provided, a unit of measure with the highest probability is determined. Each potential unit of measure is analyzed until either a list of potential units of measure is exhausted, or the weight measurement value is physiological bound as described below.

Specifically, the process receives a birth date 610 of a patient record 605 and a weight record 615 as described above. The weight record includes an encounter date 708, a weight measurement 716, and a unit of measure 728. The birth date and encounter date 708 of the patient record are utilized at step 710 to determine a patient age 712 at the time of the weight measurement (e.g., from a difference between the encounter date and the patient birth date).

Weight measurement 716 is cleansed at step 718 to produce a cleansed weight value 720. The initial cleansing removes potential items polluting the value of the weight measurement, and performs various operations to address informalities in the weight measurement (e.g., units in the improper field, typographical or other errors (e.g., inches instead of feet), non-numeric characters, commas, slashes, multiple periods, number formatting, etc.).

For example, when the weight measurement does not contain numbers, no further cleansing is provided, and the measurement format remains invalid (which is checked at step 724 described below). Comma placement may further be addressed by the cleansing. When there is an instance of a comma and a period next to each other, the whole combination is replaced by a period. If there is exactly one digit followed by a comma, the comma is replaced by a single quote (e.g., a localization error). When two or more digits are followed by a comma, the comma is replaced by a decimal point, and a comma is removed if placed next to letters.

Moreover, slashes may be handled by the initial cleansing. For example, when two digits are followed by a slash, the slash is replaced by a period (presumed to be the intent due to the proximity of the slash and period on a keyboard). However, exceptions are made when slashes are used for dates. When a date format is encountered, the date is removed. Multiple periods are typically entered inadvertently. If consecutive periods are encountered, they are replaced with a single period. When a non-digit header is encountered, the header is always removed. Similarly, numbers of the form x.y.z are truncated to a single period.

In addition, it may be possible to have non-alphanumerical characters (e.g., for height with a value X' Y"). In this case, the measurement value may be split by any non-numerical characters. If the cleansing was successful, the appropriate portion of the height values should be juxtaposed to each other.

When the format of the cleansed weight value is not valid as determined at step 724, a null value is returned for the standardized weight measurement at step 726.

Unit of measure 728 is standardized at step 730 to produce a standardized unit of measure 732. For example, the unit of measure is processed to conform to standard forms for the units of measure (e.g., pounds to lbs, kilograms to kg, centimeters to cm, accommodate different abbreviations or capitalizations, etc.). When the standardized unit of measure is not valid (e.g., a height unit of measure is employed for weight, no unit of measure is provided, etc.) as determined at step 734, another most likely unit of measure is selected from a set of units of measure based on the cleansed weight value and patient age at step 736.

The set of units of measure may be stored in a dictionary for an organization and accessed or mapped via a map file (e.g., mapping the weight records to the organization and/or set of units of measures). The set of units of measure may include members that account for different quantities. This may be utilized to accommodate errors relating to decimal point placement (e.g., a unit of measure for pounds, tens of pounds, hundreds of pounds, etc.).

The cleansed weight value and standardized unit of measure are utilized to determine whether the cleansed weight value relative to the standardized unit of measure is within a physiological region at step 714 described below (e.g., for FIGS. 8A and 8B). When the cleansed weight value is not within the physiological region, another unit of measure from the set of units of measure is selected at step 746 when additional units of measure are available as determined at step 742. Each unit of measure from the set of units of measure is processed until a unit of measure is selected to enable compliance of the cleansed weight value with the physiological region. When the units of measure from the set of units of measure have been exhausted without the cleansed weight value complying with the physiological region, a null value is returned for the standardized weight measurement at step 744. Thus, various types of inconsistencies in the cleansed weight value may be addressed based on the set of units of measure. For example, a weight value may be incorrectly entered as 18.50 pounds instead of 185.0 pounds. A unit of measure for tens of pounds may be in the set of units of measure and, when processed, enables the cleansed weight value to comply with the physiological region (e.g., effectively equating 18.5 tens of pounds to 185.0 pounds).

When the cleansed weight value is within the physiological region as determined at step 714, the cleansed weight value is converted, if needed, to correspond with a standardized unit of measure at step 738 (e.g., 18.50 tens of pounds to 185.0 pounds), and the converted weight value is returned as the standardized weight measurement at step 740.

Figure 8A:
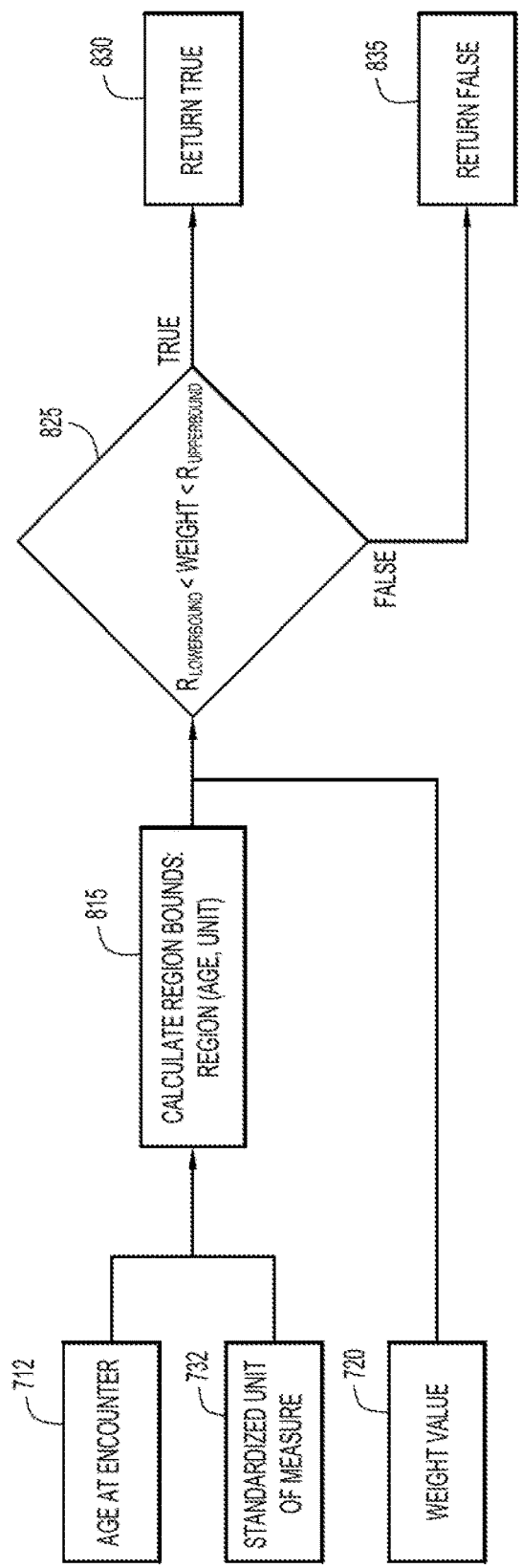
FIG. 8A is a flow diagram illustrating a manner of validating data values based on a dynamically determined physiological range according to an embodiment of the present invention.

A manner of determining whether a weight measurement is within a physiological region (e.g., via factory grid 160 and standardization module 267) according to an embodiment of the present invention (e.g., step 714 of FIG. 7) is illustrated in FIG. 8A. Initially, a physiological technique compares a patient weight value against bounds that are trained using a population data set (e.g., thereby being a population centric technique). Each data point is treated independently, and a weight value is considered in the physiological region when the weight value is strictly between dynamically calculated upper and lower bounds for a given unit of measure and patient age at the encounter. These bound values are determined from piecewise logistic and fractional polynomial functions. These functions are determined using a classification regression model. Due to the discrete nature of the units of measure, a multiclass logistic regression technique may be used. Once the boundary functions are determined, the functions may be simplified to functions with similar shapes of less order. This maintains a least amount of parameters (e.g., to avoid over-fitting, high maintenance in case of future changes, etc.). In case a unit of measure is not provided, a k-means clusterization algorithm is employed using the weight value and age of the patient at the encounter. Example physiological regions are illustrated in FIG. 8B described below.

In particular, a patient age 712 at an encounter and a standardized unit of measure 732 are utilized to determine the corresponding upper bound (e.g., $R_{UPPERBOUND}$ or $W_{HIGH}$) and lower bound (e.g., $R_{LOWERBOUND}$ or $W_{LOW}$) of the patient for a physiological region at step 815. For example, the physiological bounds are determined by calculating upper and lower bounds. The upper and lower bounds are functions dependent on the age of the patient calculated at the time of the encounter. The boundaries are initially determined using a classification regression model. Due to the discrete nature of units of measure, a multiclass logistic regression technique may be used. Once the boundary functions are determined, the functions may be simplified to functions with similar shapes of less order for maintenance purposes. The boundaries are designed to enable performance of a conservation conversion in case a unit of measure is not provided.

The upper and lower bounds, by way of example, may be determined from the following expressions derived from the above techniques (e.g., for the lower bound, $W_{LOW,\ UNIT}$, and upper bound $W_{HIGH,\ UNIT}$ based on the time, t, of the encounter, where time periods for, t, are partitioned for units of pounds and kilograms):

$$W_{LOW,OZ}(t) = 1{,}500 + (27.5 - 1{,}500)e^{-t/13}$$

$$W_{HIGH,OZ}(t) = 8{,}000 + (255 - 8{,}000)e^{-t/13}$$

$$W_{LOW,LBS}(t) = \begin{cases} t < 9;\ 2.2 + \sqrt{145.3t + 10.7} \\ t \geq 9;\ 22.0 + (90.0 - 18.0)/(1 + e^{-(t-12)/3.25}) \end{cases}$$

$$W_{HIGH,LBS}(t) = \begin{cases} t < 5;\ 17.2 + \sqrt{900.0t + 10.7} \\ t \geq 5;\ 70.0 + (500.0 - 73.0)/(1 + e^{-(t-10.5)/1.75}) \end{cases}$$

$$W_{LOW,KG}(t) = \begin{cases} t < 6;\ 1.0 + \sqrt{1.56t} \\ t \geq 6;\ 2.8 + (44.0 - 2.82)/(1 + e^{-(t-14)/2.2}) \end{cases}$$

$$W_{HIGH,KG}(t) = \begin{cases} t < 5;\ 2.2 + \sqrt{98.9t + 10.7} \\ t \geq 5;\ 18.0 + (89.0 - 18.0)/(1 + e^{-(t-12)/3.25}) \end{cases}$$

Figure 8B:
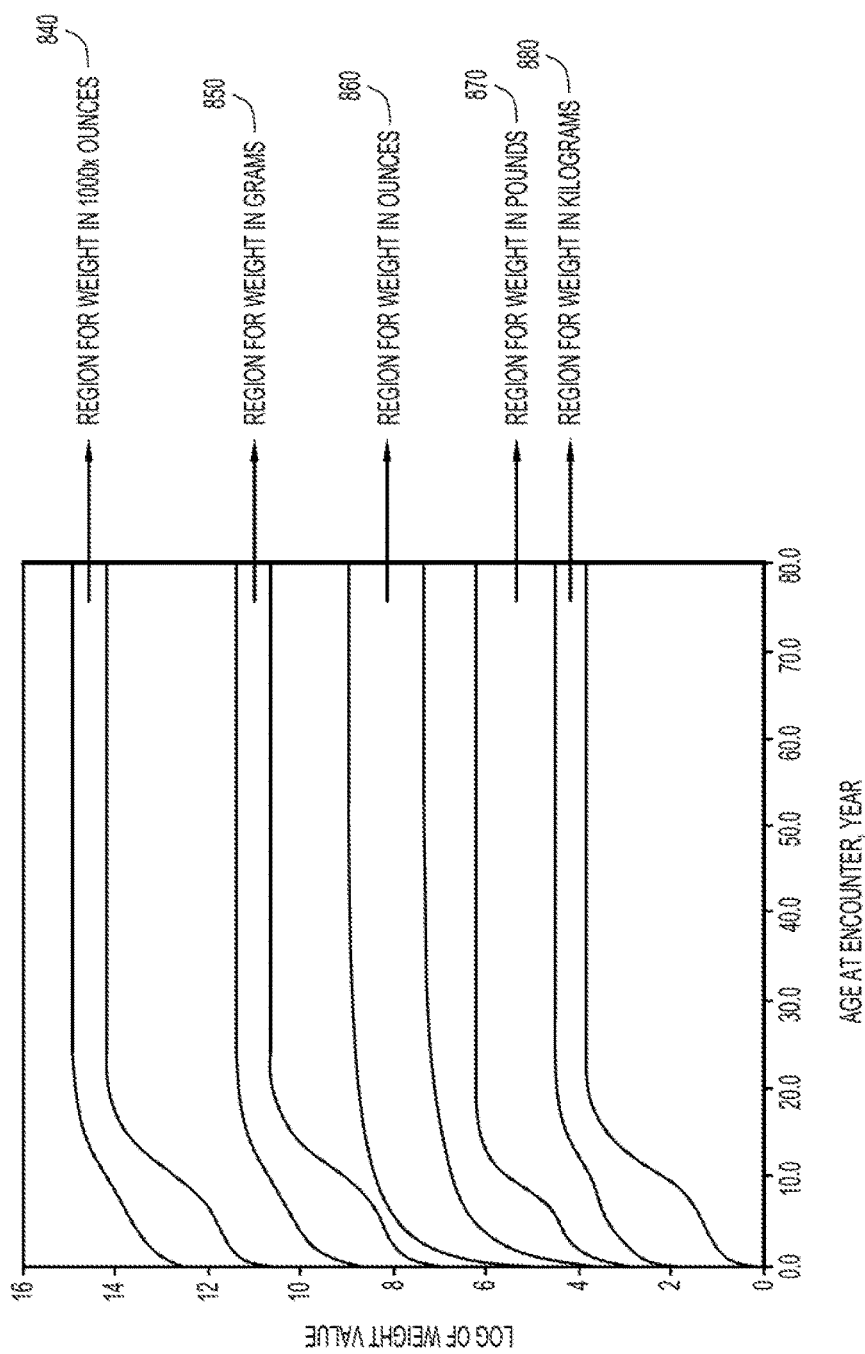
FIG. 8B is a graphical illustration of example physiological regions that may be utilized by the manner of FIG. 8A according to an embodiment of the present invention

FIG. 8B illustrates a graphical representation of a series of example physiological regions or curves 840, 850, 860, 870, and 880 plotted on an X-axis (or abscissa) representing the age of the patient at the encounter and a Y-axis (or ordinate) representing the weight value. For example: region 840 corresponds to weight values in thousands of ounces; region 850 corresponds to weight values in grams; region 860 corresponds to weight values in ounces; region 870 corresponds to weight values in pounds; and region 880 corresponds to weight values in kilograms. The bounds for the example regions may be determined by using k-means clusterization against numerous weight clinical data points (e.g., over 100 million weight clinical records). The records span multiple stages of life (e.g., birth, infant, adolescence, adulthood, geriatric, etc.). The regions are age dependent and, thus, take human growth (and shrinkage) into account. Once the regions or clusters are determined, piecewise functions may be constructed to optimize region demarcations. For example, Gauss Least Square approximation and parameter estimation techniques may be employed for linear and non-linear functions, respectively. Piecewise functions are continuous and differentiable through the domains. A log plot is illustrated solely by way of example and for display purposes in order to compensate for the large dynamic range of the regions.

Once the lower and upper bounds for the patient are determined at step 815 (FIG. 8A), cleansed weight value 720 is compared to the lower and upper bounds to determine whether the cleansed weight value lies in the corresponding physiological region defined by the bounds (e.g., the weight value is between the lower and upper bounds) at step 825. When the cleansed weight value resides within the physiological region, a corresponding positive indication (e.g., TRUE) is returned at step 830. If the cleansed weight value resides outside the physiological region, a corresponding negative indication (e.g., FALSE) is returned at step 835.

Figure 9:
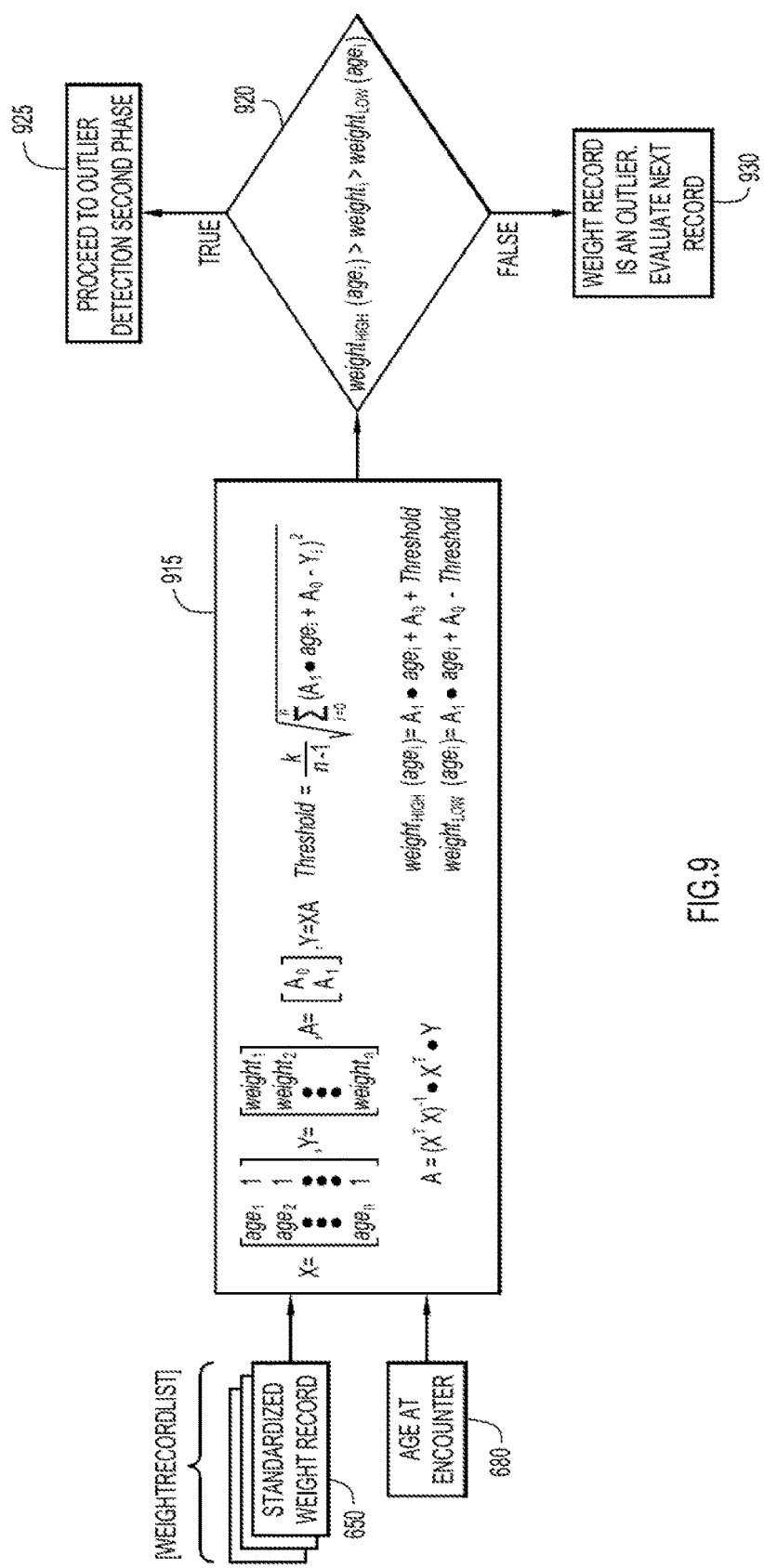
FIG. 9 is a flow diagram illustrating a manner of detecting outliers within the data values based on patient historical data according to an embodiment of the present invention.
Figure 10:
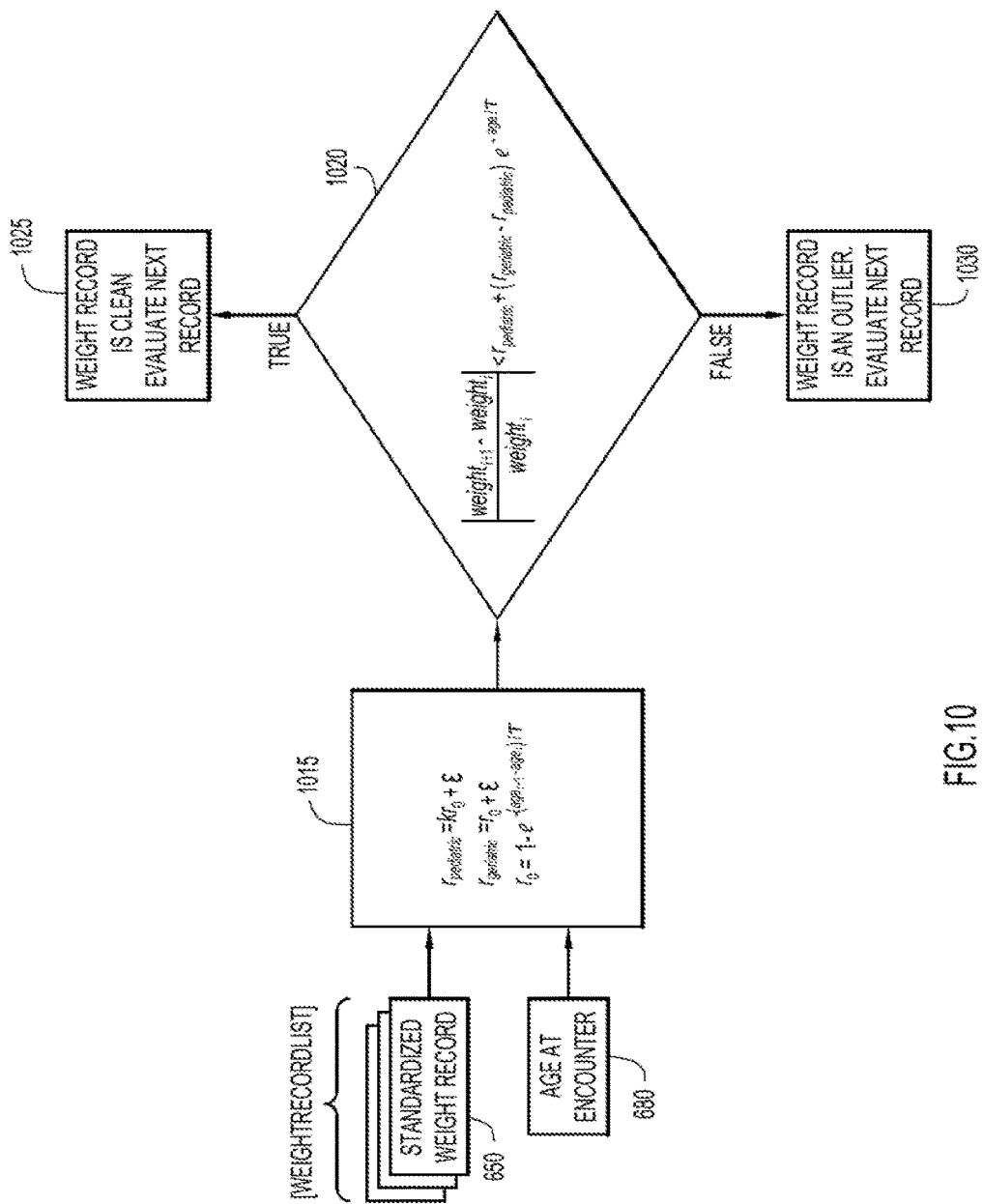
FIG. 10 is a flow diagram illustrating a manner of detecting outliers within the data values based on consecutive patient measurements according to an embodiment of the present invention.

A manner of determining whether a standardized weight measurement is an outlier (e.g., via factory grid 160 and standardization module 267) according to an embodiment of the present invention (e.g., step 655 of FIG. 6) is illustrated in FIGS. 9 and 10. Initially, outlier detection comprises different phases. A first phase (FIG. 9) constructs thresholds for each patient that are dependent on that patient historical data and used to determine upper and lower bounds defining a valid range for a weight measurement (e.g., weight values outside the range are considered outliers). Therefore, this phase is dependent on the entire set of the records for that patient (e.g., patient centric). A second phase of outlier detection (FIG. 10) examines differentials between temporally adjacent records. Since temporally adjacent records are compared, the second phase is similarly patient centric. However, the second phase includes population centric aspects since differential thresholds are determined and trained from a population data set.

In particular, a standardized weight record 650 and a patient age at an encounter 680 are utilized to dynamically determine a threshold at step 915 (FIG. 9). This threshold is utilized to generate upper and lower bounds (e.g., $WEIGHT_{HIGH}$ and $WEIGHT_{LOW}$) defining a valid range for the specific patient for a first phase of the outlier detection. For example, the dynamic threshold used to determine the upper and lower bounds (e.g., $WEIGHT_{HIGH}$ and $WEIGHT_{LOW}$) is calculated for a patient for the first phase of the outlier detection using a Gauss Least Square technique on a first order polynomial. The threshold is linearly dependent on the patient age and the variance between the model and the patient weight data. A multiple of the variance (e.g., forming the threshold) is added or subtracted from the model to determine the upper bound (e.g., $WEIGHT_{HIGH}$) and lower bound (e.g., $WEIGHT_{LOW}$), respectively. The upper and lower limits are therefore parallel to the model and bound to a dynamic range for that particular patient.

By way of example, the dynamic threshold and upper and lower bounds (e.g., $WEIGHT_{HIGH}$ and $WEIGHT_{LOW}$) may be determined from the following expressions:

$$X = \begin{bmatrix} age_1 & 1 \\ age_2 & 1 \\ \vdots & \\ age_n & 1 \end{bmatrix};\ Y = \begin{bmatrix} weight_1 \\ weight_2 \\ \vdots \\ weight_n \end{bmatrix};$$

$$A = (X^T X)^{-1} \cdot X^T \cdot Y;\ A = \begin{bmatrix} A_0 \\ A_1 \end{bmatrix};\ Y = XA$$

$$\text{Threshold} = \frac{k}{n-1} \sqrt{\sum_{i=0}^{n} (A_1 \cdot age_i + A_0 - Y_i)^2}$$

$$WEIGHT_{HIGH}(age_i) = A_1 \cdot age_i + A_0 + \text{Threshold}$$

$$WEIGHT_{LOW}(age_i) = A_1 \cdot age_i + A_0 - \text{Threshold}$$

where the age and weight values are determined from the patient records and the A matrix is updated based on data from new or additional records, n indicates a quantity of measurements, and k is a multiplier derived from analysis and training of the model based on weight data of the population. The multiplier, k, controls the sensitivity of the detection to outliers (e.g., the number of increments of the variance for the threshold to determine the range for the weight values).

Once the dynamic threshold and upper and lower bounds are determined for the patient at step 915, the standardized weight measurement of the standardized weight record is compared to the upper and lower bounds (e.g., $WEIGHT_{HIGH}$ and $WEIGHT_{LOW}$) (e.g., to determine whether the standardized weight measurement lies in the corresponding valid range defined by the bounds (e.g., the weight measurement is between the lower and upper bounds)) at step 920. When the standardized weight measurement resides within the valid range, the second phase of the outlier detection is performed (FIG. 10) for further validation at step 925 as described below. If the standardized weight measurement resides outside the valid range, the standardized weight measurement is indicated as an outlier (or erroneous), and a subsequent standardized weight record is processed at step 930.

Referring to FIG. 10, once a standardized weight measurement of a standardized weight record 650 is within the valid range as determined at step 925 (FIG. 9), the second phase of outlier detection is initiated. Initially, this phase of outlier detection considers the gradient between temporally successive records. If a sudden change between two weight records occurs, the record is considered to be an outlier. This compensates for the situation where certain records have valid physiological values, but may have been entered incorrectly. For example, three weight records for a given patient may include: a first weight record of 180 lbs; a second weight record of 480 lbs one month after the first weight record; and a third weight record of 185 lbs a month after the second weight record. Although these three records may be within the physiological bounds, the first phase of the outlier detection may fail to recognize the second weight record of 480 lbs as an outlier since this patient only has three records. Accordingly, the outlier holds significant weight in determining the dynamic values. This type of error is typically common (e.g., since the "1" and "4" digits are very close to each other on a number pad (e.g., 480 lbs entered instead of 180 lbs)). This phase of outlier detection determines physiological ranges for weight differentials. In particular, when a large growth or reduction happened in a short amount of time, the record is considered to be an outlier.

In particular, a standardized weight record 650 satisfying the validation range of the first phase of outlier detection and a corresponding patient age 680 at a time of encounter are utilized to dynamically determine various rates of growth based on the patient age and data from a population at step 1015 (FIG. 10). The rates of growth include a geriatric rate of growth, $r_{geriatric}$, and a pediatric rate of growth, $r_{pediatric}$. These rates of growth are utilized to determine limits for the second phase of the outlier detection.

The rates of growth may be determined based on a gradient descent technique applied to the population data. By way of example, the rates of growth may be determined from the following expressions:

$$r_0 = 1 - e^{-(age_{i+1} - age_i)/\tau}$$

$$r_{geriatric} = r_0 + \varepsilon$$

$$r_{pediatric} = kr_0 + \varepsilon$$

where $age_i$ and $age_{i+1}$ represent the age of the patient at consecutive encounters (e.g., from the current standardized weight record and a temporally adjacent standardized weight record), $r_0$ represents an initial adult rate of growth based on gradient descent of the population data, $r_{geriatric}$ represents the rate of growth for an adult, $r_{pediatric}$ represents the rate of growth for a child, $\varepsilon$ is an error term derived from the population data, and $\tau$ is a rate of convergence of the growth rates. The rate of growth for an adult is based on the initial growth rate and an error term. The pediatric growth rate is modeled as a multiple of the adult growth rate (since children grow faster than adults) with an additional error term.

Once the rates of growth are determined for the patient at step 1015, the standardized weight measurements of the standardized weight record and a temporally adjacent standardized weight record are utilized for a comparison with a combination of the rates of growth at step 1020. In particular, the standardized weight measurements may be combined to form a ratio of the difference between the standardized weight measurements of the temporally adjacent standardized weight records with respect to the current standardized weight measurement. For example, the ratio may be expressed as:

$$\frac{Weight(t_{i+1}) - Weight(t_i)}{Weight(t_i)}$$

where $Weight(t_{i+1})$ represents the subsequent standardized weight measurement and $Weight(t_i)$ represents the current standardized weight measurement.

The geriatric and pediatric rates of growth are combined to form a limit. This may be expressed as:

$$r_{pediatric} + (r_{geriatric} - r_{pediatric})e^{-age_i/\tau}$$

where $age_i$ represent the age of the patient at the current encounter (e.g., from the current standardized weight record), $r_{geriatric}$ represents the rate of growth for an adult, $r_{pediatric}$ represents the rate of growth for a child, and $\tau$ is a rate of convergence of the growth rates. By way of example only, the rates of growth for a population may include $r_{pediatric} = 0.2106$, $r_{geriatric} = 11.160$, and $\tau = 7.0$. However, any suitable values based on any populations of data may be utilized.

The ratio of standardized weight measurements is compared to the limit formed by the arrangement of growth rates. By way of example, this may be expressed as:

$$\frac{Weight(t_{i+1}) - Weight(t_i)}{Weight(t_i)} < r_{pediatric} + (r_{geriatric} - r_{pediatric})e^{-age_i/\tau}$$

where $Weight(t_{i+1})$ represents the subsequent standardized weight measurement, $Weight(t_i)$ represents the current standardized weight measurement, $age_i$ represent the age of the patient at the current encounter (e.g., from the current standardized weight record), $r_{geriatric}$ represents the rate of growth for an adult, $r_{pediatric}$ represents the rate of growth for a child, and $\tau$ is a rate of convergence of the growth rates.

When the standardized weight measurement satisfies the limit, the standardized weight record is considered clean or valid at step 1025, and a subsequent standardized weight record is retrieved for processing in the first phase of outlier detection (FIG. 9) as described above. If the standardized weight measurement fails to satisfy the limit, the standardized weight record is indicated as an outlier (or erroneous) at step 1030, and a subsequent standardized weight record is retrieved for processing in the first phase of outlier detection (FIG. 9) as described above. The process for FIGS. 9 and 10 is repeated until each of the standardized weight records 650 has been processed.

Figure 11:
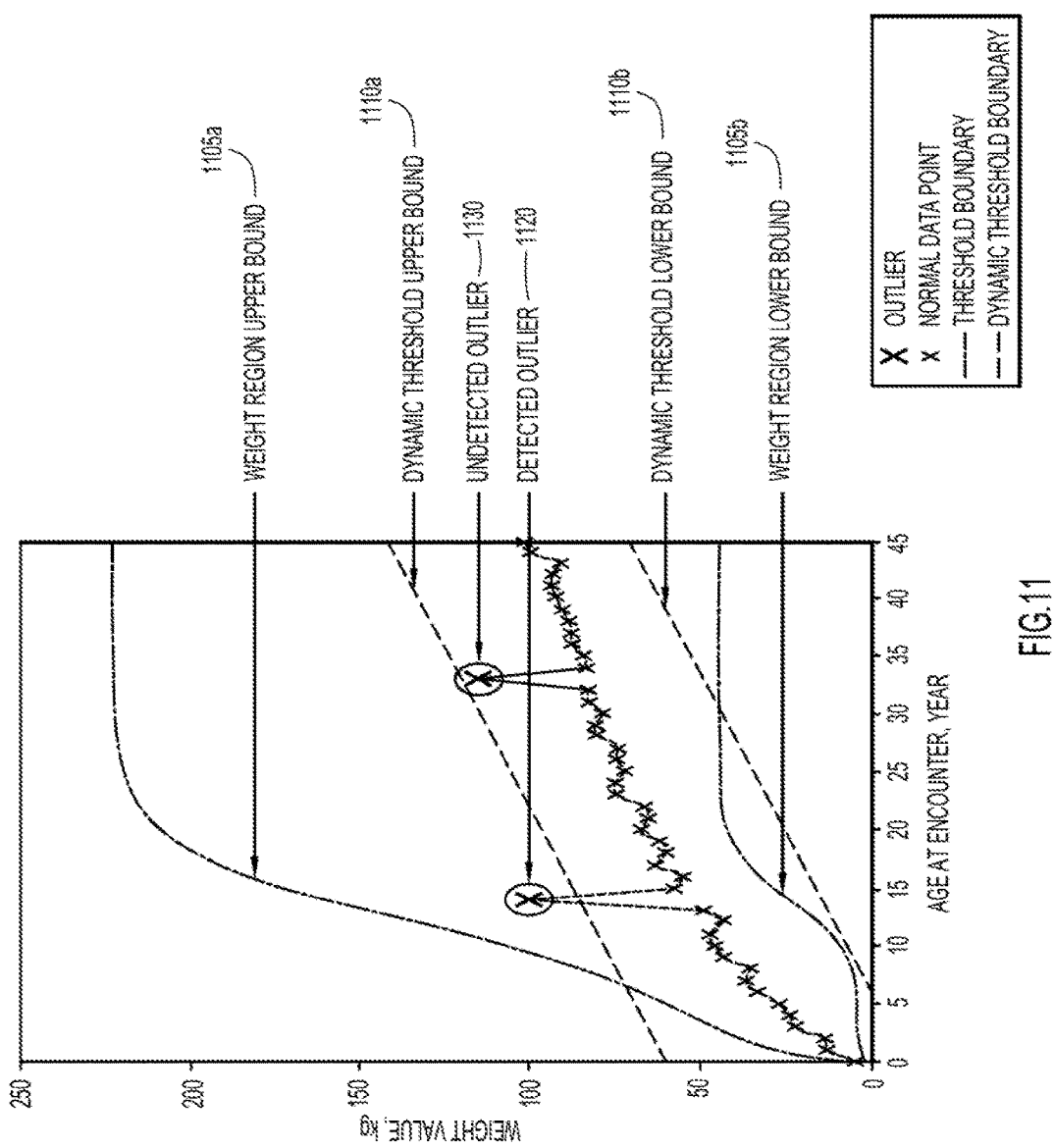
FIG. 11 is a graphical illustration of an example performance of the outlier detection of FIG. 9 according to an embodiment of the present invention.

Example results of performance of the first phase of outlier detection are illustrated in FIG. 11. Specifically, the example graph indicates age on the X-axis (or abscissa) and weight values on the Y-axis (or ordinate). Dashed boundary lines 1105a and 1105b represent the upper bound ($R_{UPPERBOUND}$) and lower bound ($R_{LOWERBOUND}$) of the physiological region described above (e.g., for FIGS. 8A and 8B).

Dashed boundary lines 1110a and 1110b represent the upper bound ($WEIGHT_{HIGH}$) and lower bound ($WEIGHT_{LOW}$) of the valid region produced by the first phase of the outlier detection described above (e.g., for FIG. 9). Even though a weight record may be within the physiological region, this record may still be considered an outlier. For example, data point 1120 (e.g., at age 14) resides within the physiological region defined by lines 1105a and 1105b and, therefore, is not initially detected as an outlier by the physiological validation. However, this data point does reside outside the valid range of the first phase of the outlier detection defined by lines 1110a and 1110b and, consequently, is ultimately detected as an outlier during the first phase of outlier detection. Data point 1130 (e.g., at age 33) resides within the physiological region defined by lines 1105a and 1105b, and the valid range defined by lines 1110a and 1110b and, therefore, is not initially detected as an outlier by the physiological validation nor the first phase of outlier detection. However, the second phase of the outlier detection may detect this outlier as described below.

Figure 12:
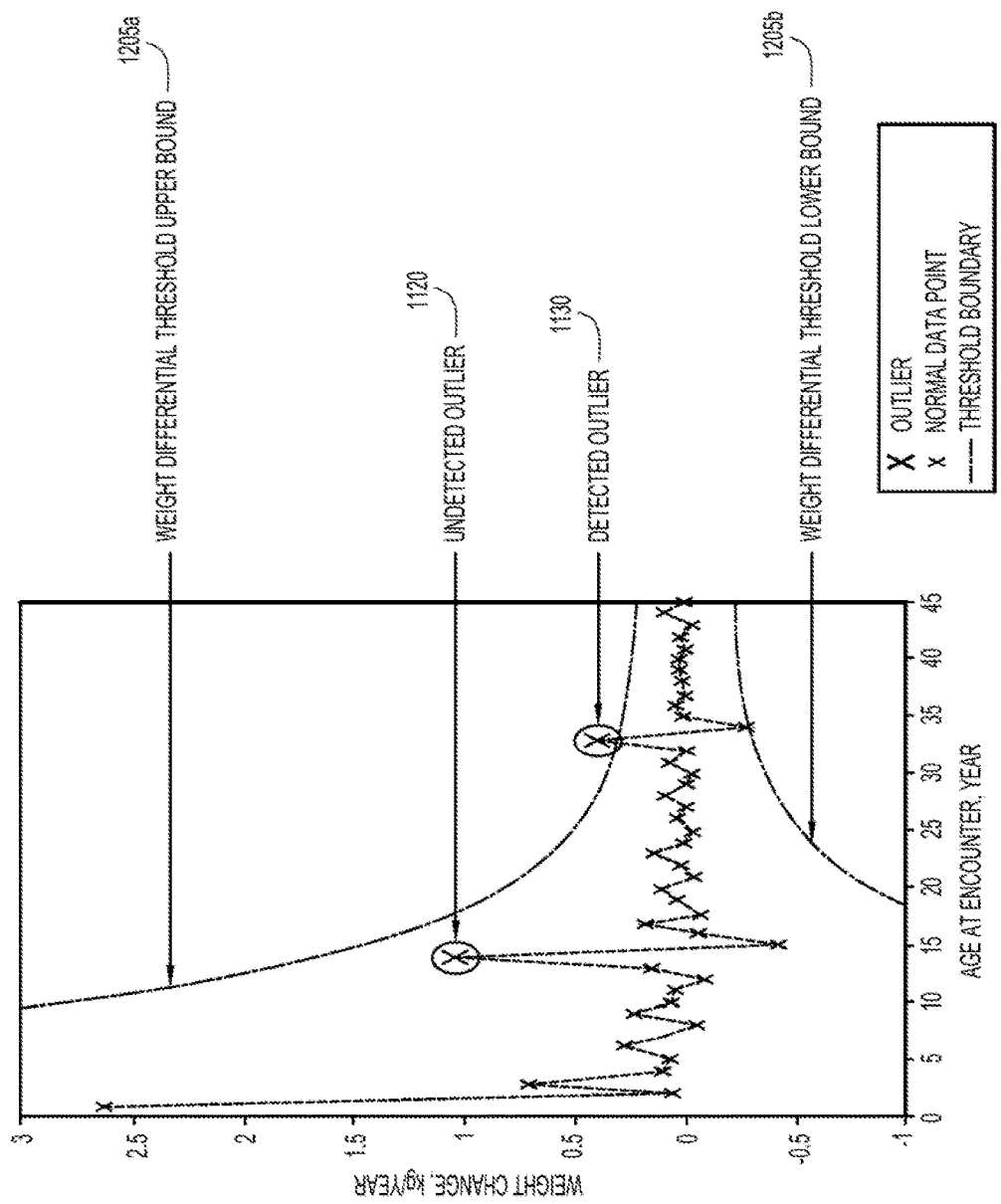
FIG. 12 is a graphical illustration of an example performance of the outlier detection of FIG. 10 according to an embodiment of the present invention.

Example results of performance of the second phase of outlier detection are illustrated in FIG. 12. Specifically, the example graph indicates age on the X-axis (or abscissa) and change in weight values on the Y-axis (or ordinate). Dashed boundary lines 1205a and 1205b represent the valid region defined by the rates of growth described above (e.g., for FIG. 10). For example, data point 1120 (e.g., at age 14) resides within the valid region defined by lines 1205a and 1205b and, therefore, would not be detected as an outlier by the second phase of outlier detection. However, data point 1120 does reside outside the valid range of the first phase of the outlier detection defined by lines 1110a and 1110b (FIG. 11) and, consequently would be detected as an outlier during that first phase as described above.

Data point 1130 (e.g., at age 33) resides within the physiological region defined by lines 1105a and 1105b (FIG. 11), and the valid range defined by lines 1110a and 1110b and, therefore, is not initially detected as an outlier by the physiological validation nor the first phase of outlier detection as discussed above. However, this data point does reside outside the valid region defined by lines 1205a and 1205b, and is ultimately detected as an outlier by the second phase of the outlier detection.

The examples of FIGS. 11-12 illustrate the complementary and compensatory nature of the physiological validation and individual outlier detection phases. For example, data point 1120 satisfies the physiological validation and second phase of outlier detection, but would be detected by the first phase of outlier detection. Similarly, data point 1130 satisfies the physiological validation and first phase of outlier detection, but would be detected by the second phase of outlier detection. The physiological validation and individual outlier detection phases may be employed individually (without the others), or in any combination.

It will be appreciated that the embodiments described above and illustrated in the drawings represent only a few of the many ways of implementing embodiments for data standardization and validation across different data systems.

The environment of the present invention embodiments may include any number of computer or other processing systems (e.g., client or end-user systems, server systems, etc.) and databases or other repositories arranged in any desired fashion, where the present invention embodiments may be applied to any desired type of computing environment (e.g., cloud computing, client-server, network computing, mainframe, stand-alone systems, etc.). The computer or other processing systems employed by the present invention embodiments may be implemented by any number of any personal or other type of computer or processing system (e.g., desktop, laptop, PDA, mobile devices, etc.), and may include any commercially available operating system and any combination of commercially available and custom software (e.g., browser software, communications software, server software, standardization module, etc.). These systems may include any types of monitors and input devices (e.g., keyboard, mouse, voice recognition, etc.) to enter and/or view information.

It is to be understood that the software (e.g., standardization module, etc.) of the present invention embodiments may be implemented in any desired computer language and could be developed by one of ordinary skill in the computer arts based on the functional descriptions contained in the specification and flow charts illustrated in the drawings. Further, any references herein of software performing various functions generally refer to computer systems or processors performing those functions under software control. The computer systems of the present invention embodiments may alternatively be implemented by any type of hardware and/or other processing circuitry.

The various functions of the computer or other processing systems may be distributed in any manner among any number of software and/or hardware modules or units, processing or computer systems and/or circuitry, where the computer or processing systems may be disposed locally or remotely of each other and communicate via any suitable communications medium (e.g., LAN, WAN, Intranet, Internet, hardwire, modem connection, wireless, etc.). For example, the functions of the present invention embodiments may be distributed in any manner among the various end-user/client and server systems, and/or any other intermediary processing devices. The software and/or algorithms described above and illustrated in the flow charts may be modified in any manner that accomplishes the functions described herein. In addition, the functions in the flow charts or description may be performed in any order that accomplishes a desired operation.

The software of the present invention embodiments (e.g., standardization module, etc.) may be available on a non-transitory computer useable medium (e.g., magnetic or optical mediums, magneto-optic mediums, floppy diskettes, CD-ROM, DVD, memory devices, etc.) of a stationary or portable program product apparatus or device for use with stand-alone systems or systems connected by a network or other communications medium.

The communication network may be implemented by any number of any type of communications network (e.g., LAN, WAN, Internet, Intranet, VPN, etc.). The computer or other processing systems of the present invention embodiments may include any conventional or other communications devices to communicate over the network via any conventional or other protocols. The computer or other processing systems may utilize any type of connection (e.g., wired, wireless, etc.) for access to the network. Local communication media may be implemented by any suitable communication media (e.g., local area network (LAN), hardwire, wireless link, Intranet, etc.).

The system may employ any number of any conventional or other databases, data stores or storage structures (e.g., files, databases, data structures, data or other repositories, etc.) to store information (e.g., standardized forms, outlier records or lists, valid records or lists, bounds, thresholds, etc.). The database system may be implemented by any number of any conventional or other databases, data stores or storage structures (e.g., files, databases, data structures, data or other repositories, etc.) to store information. The database system may be included within or coupled to the server and/or client systems. The database systems and/or storage structures may be remote from or local to the computer or other processing systems, and may store any desired data.

The present invention embodiments are not limited to the specific tasks or algorithms described above, but may be utilized for standardizing and validating any type of physiological or other attributes, especially those having valid ranges varying over time. For example, the present invention embodiments may be utilized to validate any suitable physiological attributes (e.g., height, weight, head circumference or other body measurements, etc.) or other attributes that may have varying valid values or ranges over time. Further, present invention embodiments may process any types of data or data records from any suitable data sources (e.g., medical, financial, employment, public records, etc.).

The present invention embodiments may utilize any types of populations (e.g., patient or other groups, etc.) having any desired criteria for inclusion of members. The populations may include any desired quantity of records or data. The present invention embodiments may employ various conventional or other techniques to analyze the population data to determine the models, thresholds, and bounds for the physiological validation and outlier detection (e.g., Gauss Least Squares, regression modeling, clustering, parameter estimation, curve fitting, etc.). The expressions and corresponding parameter values described above may be modified in any fashion based on the data of a particular population and/or the analysis techniques employed. The attribute values may be compared to the bounds in any desired fashion (e.g., greater than less than, greater than or equal to, less than or equal to, exclusive of the range, inclusive of the range, etc.).

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises", "comprising", "includes", "including", "has", "have", "having", "with" and the like, when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A computer-implemented method in a data processing system comprising at least one processor and at least one memory, the at least one memory comprising instructions executed by the at least one processor to cause the at least one processor to standardize and validate data across source systems, the computer-implemented method comprising:
   converting a value of a physiological attribute of an entity to a standardized value;
   dynamically determining a plurality of value ranges for the physiological attribute, wherein a first value range is determined from population centric information including physiological data of a population, and wherein one or more second value ranges are determined from entity centric information including a history of physiological attribute values of the entity and corresponding ages of the entity;
   comparing the standardized value of the physiological attribute to the plurality of value ranges; and
   designating the standardized value of the physiological attribute as an outlier in response to the standardized value of the physiological attribute residing outside of one or more of the first value range and an individual second value range.

2. The computer-implemented method of claim 1, wherein the entity includes a patient, and the physiological attribute includes one or more selected from a group of height and weight.

3. The computer-implemented method of claim 1, wherein dynamically determining the plurality of value ranges further comprises:
   dynamically determining a second value range for the physiological attribute from the history of physiological attribute values of the entity and corresponding ages of the entity, wherein the second value range is specific to and varies with the age of the entity; and
   comparing the standardized value of the physiological attribute further comprises:
   in response to the standardized value of the physiological attribute residing within the first value range, comparing the standardized value of the physiological attribute to the second value range.

4. The computer-implemented method of claim 3, wherein dynamically determining the plurality of value ranges further comprises:
   dynamically determining a third value range for the physiological attribute based on a difference between temporally adjacent measurements of values for the physiological attribute; and
   comparing the standardized value of the physiological attribute further comprises:
   in response to the standardized value of the physiological attribute residing within the second value range, comparing the standardized value of the physiological attribute to the third value range.

5. The computer-implemented method of claim 1, further comprising:
   retrieving the value of the physiological attribute from one or more medical records of the entity.

6. The computer-implemented method of claim 1, wherein the standardized value for the physiological attribute is associated with a unit of measure, and comparing the standardized value of the physiological attribute further comprises:

changing the unit of measure to another unit of measure from among a set of units of measure in response to the standardized value with the unit of measure residing outside the first value range.

7. A system for standardizing and validating data across source systems comprising:

at least one processor configured to:

convert a value of a physiological attribute of an entity to a standardized value;

dynamically determine a plurality of value ranges for the physiological attribute, wherein a first value range is determined from population centric information including physiological data of a population, and wherein one or more second value ranges are determined from entity centric information including a history of physiological attribute values of the entity and corresponding ages of the entity;

compare the standardized value of the physiological attribute to the plurality of value ranges; and designate the standardized value of the physiological attribute as an outlier in response to the standardized value of the physiological attribute residing outside of one or more of the first value range and an individual second value range.

8. The system of claim 7, wherein the entity includes a patient, and the physiological attribute includes one or more selected from a group of height and weight.

9. The system of claim 7, wherein dynamically determining the plurality of value ranges further comprises:

dynamically determining a second value range for the physiological attribute from the history of physiological attribute values of the entity and corresponding ages of the entity, wherein the second value range is specific to and varies with the age of the entity; and comparing the standardized value of the physiological attribute further comprises:

in response to the standardized value of the physiological attribute residing within the first value range, comparing the standardized value of the physiological attribute to the second value range.

10. The system of claim 9, wherein dynamically determining the plurality of value ranges further comprises:

dynamically determining a third value range for the physiological attribute based on a difference between temporally adjacent measurements of values for the physiological attribute; and comparing the standardized value of the physiological attribute further comprises:

in response to the standardized value of the physiological attribute residing within the second value range, comparing the standardized value of the physiological attribute to the third value range.

11. The system of claim 7, wherein the at least one processor is further configured to:

retrieve the value of the physiological attribute from one or more medical records of the entity.

12. The system of claim 7, wherein the standardized value for the physiological attribute is associated with a unit of measure, and comparing the standardized value of the physiological attribute further comprises:

changing the unit of measure to another unit of measure from among a set of units of measure in response to the standardized value with the unit of measure residing outside the first value range.

13. A computer program product for standardizing and validating data across source systems, the computer program product comprising a computer readable storage medium having program instructions embodied therewith, the program instructions executable by at least one processor to cause the at least one processor to:

convert a value of a physiological attribute of an entity to a standardized value;

dynamically determine a plurality of value ranges for the physiological attribute, wherein a first value range is determined from population centric information including physiological data of a population, and wherein one or more second value ranges are determined from entity centric information including a history of physiological attribute values of the entity and corresponding ages of the entity;

compare the standardized value of the physiological attribute to the plurality of value ranges; and designate the standardized value of the physiological attribute as an outlier in response to the standardized value of the physiological attribute residing outside of one or more of the first value range and an individual second value range.

14. The computer program product of claim 13, wherein the entity includes a patient, and the physiological attribute includes one or more selected from a group of height and weight.

15. The computer program product of claim 13, wherein dynamically determining the plurality of value ranges further comprises:

dynamically determining a second value range for the physiological attribute from the history of physiological attribute values of the entity and corresponding ages of the entity, wherein the second value range is specific to and varies with the age of the entity; and comparing the standardized value of the physiological attribute further comprises:

in response to the standardized value of the physiological attribute residing within the first value range, comparing the standardized value of the physiological attribute to the second value range.

16. The computer program product of claim 15, wherein dynamically determining the plurality of value ranges further comprises:

dynamically determining a third value range for the physiological attribute based on a difference between temporally adjacent measurements of values for the physiological attribute; and comparing the standardized value of the physiological attribute further comprises:

in response to the standardized value of the physiological attribute residing within the second value range, comparing the standardized value of the physiological attribute to the third value range.

17. The computer program product of claim 13, wherein the at least one processor is further caused to:

retrieve the value of the physiological attribute from one or more medical records of the entity.

18. The computer program product of claim 13, wherein the standardized value for the physiological attribute is associated with a unit of measure, and comparing the standardized value of the physiological attribute further comprises:

changing the unit of measure to another unit of measure from among a set of units of measure in response to the standardized value with the unit of measure residing outside the first value range.

\* \* \* \* \*